US012582798B2

(12) United States Patent　(10) Patent No.:　US 12,582,798 B2
Kanou　(45) Date of Patent:　Mar. 24, 2026

(54) CRIMPING DEVICE AND SHAFT MANUFACTURING METHOD

(71) Applicant: TERUMO KABUSHIKI KAISHA, Tokyo (JP)

(72) Inventor: Takuo Kanou, Fujinomiya-city (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 19/189,425

(22) Filed: Apr. 25, 2025

(65) Prior Publication Data

US 2025/0332376 A1　Oct. 30, 2025

(30) Foreign Application Priority Data

Apr. 26, 2024　(JP) ................................. 2024-072765

(51) Int. Cl.
*A61M 25/00*　(2006.01)
(52) U.S. Cl.
CPC ............................... *A61M 25/0009* (2013.01)
(58) Field of Classification Search
CPC .............. B21D 39/04; Y10T 29/53522; A61B 17/06004
See application file for complete search history.

(56) References Cited

U.S. PATENT DOCUMENTS 11,027,931 B1 * 6/2021 Warriner ................ B65G 65/44

* cited by examiner

*Primary Examiner* — Jason L Vaughan
*Assistant Examiner* — Amanda Kreiling
(74) *Attorney, Agent, or Firm* — Buchanan Ingersoll & Rooney PC

(57) ABSTRACT

A crimping device for crimping a cylindrical body to a shaft member for a catheter, includes: a first crimping member configured to perform first crimping to obtain a first crimped state; a positioning member configured to perform a positioning operation, the positioning operation including: a radial operation; and a retaining operation, the radial operation being to be performed to obtain a contact state where the cylindrical body has a rear end face in contact with the positioning member, the retaining operation being to be performed to obtain a positioned state where the cylindrical body is positioned to the shaft member after the shaft member moves backward with respect to the cylindrical body in the contact state; and a second crimping member that performs second crimping to obtain a second crimped state where the cylindrical body is crimped more firmly than the cylindrical body in the first crimped state.

20 Claims, 7 Drawing Sheets

CRIMPING DEVICE AND SHAFT MANUFACTURING METHOD

CROSS-REFERENCES TO RELATED APPLICATIONS

This application claims priority to Japanese Application No. 2024-072765 filed on Apr. 26, 2024, the entire content of which is incorporated herein by reference.

TECHNOLOGICAL FIELD

The present disclosure relates to a crimping device and a shaft manufacturing method.

BACKGROUND DISCUSSION

A crimping device for crimping a cylindrical body to a shaft member for a catheter is known (see, for example, U.S. Pat. No. 11,027,931 B1).

SUMMARY

An object of the present disclosure is to provide a crimping device and a shaft manufacturing method excellent in accuracy of a securing position for securing a cylindrical body to a shaft member for a catheter.

An aspect of the present disclosure is as follows.

[1] A crimping device for crimping a cylindrical body to a shaft member for a catheter, the crimping device including: a first crimping member configured to perform first crimping to obtain a first crimped state where the cylindrical body is crimped to the shaft member with the cylindrical body that has the shaft member inserted through the cylindrical body and is fastened in a radial direction of the cylindrical body; a positioning member configured to perform a positioning operation, the positioning member being provided ahead of the first crimping member with a movement path maintained for axially forward movement or axially backward movement of the shaft member, the positioning operation including: a radial operation in which the positioning member operates radially inwardly; and a retaining operation that retains a position of the positioning member after the radial operation, the radial operation being to be performed to obtain a contact state where the cylindrical body has a rear end face in contact with the positioning member in a case where the rear end face of the cylindrical body in the first crimped state moves backward after passing the positioning member forward, the retaining operation being to be performed to obtain a positioned state where the cylindrical body is positioned to the shaft member after the shaft member moves backward with respect to the cylindrical body in the contact state; and a second crimping member provided ahead of the positioning member with the movement path maintained, the second crimping member being configured to perform second crimping to obtain a second crimped state where the cylindrical body is crimped more firmly than the cylindrical body in the first crimped state, with the cylindrical body in the positioned state and in the contact state that is fastened in the radial direction of the cylindrical body.

[2] The crimping device according to [1], in which the positioning member includes a restricting portion that has contact with a front end face of the cylindrical body such that an inclination of the cylindrical body is restricted with respect to the shaft member when the shaft member moves forward to be inserted into the cylindrical body.

[3] The crimping device according to [2], in which the restricting portion includes a chamfered portion having a diameter decreasing forward.

[4] The crimping device according to [3], in which the positioning member is provided such that the restricting portion has contact with an entire circumference of the cylindrical body.

[5] The crimping device according to [3] or [4], in which the restricting portion of the positioning member is provided to have contact with at least two parts in a circumferential direction of the cylindrical body.

[6] The crimping device according to [5], in which the at least two parts with which the restricting portion of the positioning member is to have contact are located at regular intervals in the circumferential direction of the cylindrical body.

[7] The crimping device according to any one of [1] to [6], further including a guide member disposed behind the first crimping member, the guide member having a guide face that guides a front end of the shaft member into the cylindrical body when the shaft member moves forward.

[8] The crimping device according to [7], in which the guide face is frustoconical in shape and has a diameter decreasing forward.

The crimping device according to any one of [1] to [8], wherein the cylindrical body is a marker made of a material that is non-transmissive to X-rays.

[10] A shaft manufacturing method for manufacturing a shaft including the shaft member for the catheter and the cylindrical body crimped to the shaft member using the crimping device according to any one of [1] to [9], the method including: a first crimping step of performing the first crimping by the first crimping member; a positioning step of performing the positioning operation by the positioning member; and a second crimping step of performing the second crimping by the second crimping member.

[11] The shaft manufacturing method according to [10], further including an inserting step of moving the shaft member forward to insert the shaft member into the cylindrical body before the first crimping step, in which the positioning member includes a restricting portion that has contact with a front end face of the cylindrical body such that an inclination of the cylindrical body is restricted with respect to the shaft member in the inserting step.

[12] A crimping device for crimping a cylindrical body to a shaft member for a catheter, includes: a first crimping member configured to perform first crimping to obtain a first crimped state; a positioning member configured to perform a positioning operation, the positioning operation including: a radial operation; and a retaining operation, the radial operation being to be performed to obtain a contact state where the cylindrical body has a rear end face in contact with the positioning member, the retaining operation being to be performed to obtain a positioned state where the cylindrical body is positioned to the shaft member after the shaft member moves backward with respect to the cylindrical body in the contact state; and a second crimping member that performs second crimping to obtain a second crimped state where the cylindrical body is crimped more firmly than the cylindrical body in the first crimped state.

[13] A crimping device is disclosed for crimping a cylindrical body of a non-transmissive material to X-rays to a shaft member for a catheter, the crimping device comprising: a first crimping member, the first crimping member including a first portion and a second portion configured to perform a first crimping where the cylindrical body is crimped to the shaft member to obtain a first crimped state;

a positioning member, the positioning member including a first portion and a second portion configured to the cylindrical body on the shafter member; and a second crimping member, the second crimping member including a first portion and a second portion configured to perform a second crimping of the cylindrical body to the shaft member, and wherein the second crimping of the cylindrical body is performed after the first crimping of the cylindrical body to obtain a second crimped state.

[14] A method is disclosed for manufacturing a shaft including a shaft member for a catheter and a cylindrical body crimped to the shaft member, the method comprising: performing a first crimping of the cylindrical body to the shaft member to obtain a first crimped state where the cylindrical body is crimped to the shaft member with the cylindrical body that has the shaft member inserted through the cylindrical body and is fastened in a radial direction of the cylindrical body; performing a positioning operation with a positioning member that is arranged ahead of the first crimping member with a movement path for axially forward movement or axially backward movement of the shaft member, the positioning operation including: a radial operation in which the positioning member operates radially inwardly; and a retaining operation that retains a position of the positioning member after the radial operation, the radial operation being to be performed to obtain a contact state where the cylindrical body has a rear end face in contact with the positioning member in a case where the rear end face of the cylindrical body in the first crimped state moves backward after passing the positioning member forward, the retaining operation being to be performed to obtain a positioned state where the cylindrical body is positioned to the shaft member after the shaft member moves backward with respect to the cylindrical body in the contact state; and performing a second crimping operation with a second crimping member provided ahead of the positioning member with the movement path, the second crimping member being configured to perform a second crimping to obtain a second crimped state where the cylindrical body is crimped more firmly than the cylindrical body in the first crimped state, with the cylindrical body in the positioned state and in the contact state that is fastened in the radial direction of the cylindrical body.

According to the present disclosure, provided can be a crimping device and a shaft manufacturing method excellent in accuracy of a securing position for securing a cylindrical body to a shaft member for a catheter.

BRIEF DESCRIPTION OF THE DRAWINGS

FIG. 1 is a sectional view illustrating a state in the middle of an inserting step of a shaft manufacturing method using a crimping device according to an embodiment of the present disclosure.

FIG. 2 is a sectional view illustrating a state where the inserting step is complete after the state in FIG. 1.

FIG. 5 is a sectional view illustrating a state where a radial operation is complete in the positioning step after the state in FIG. 4.

DETAILED DESCRIPTION

Set forth below with reference to the accompanying drawings is a detailed description of embodiments of a crimping device and a shaft manufacturing method representing examples of the inventive crimping device and shaft manufacturing method disclosed here.

Figure 1:
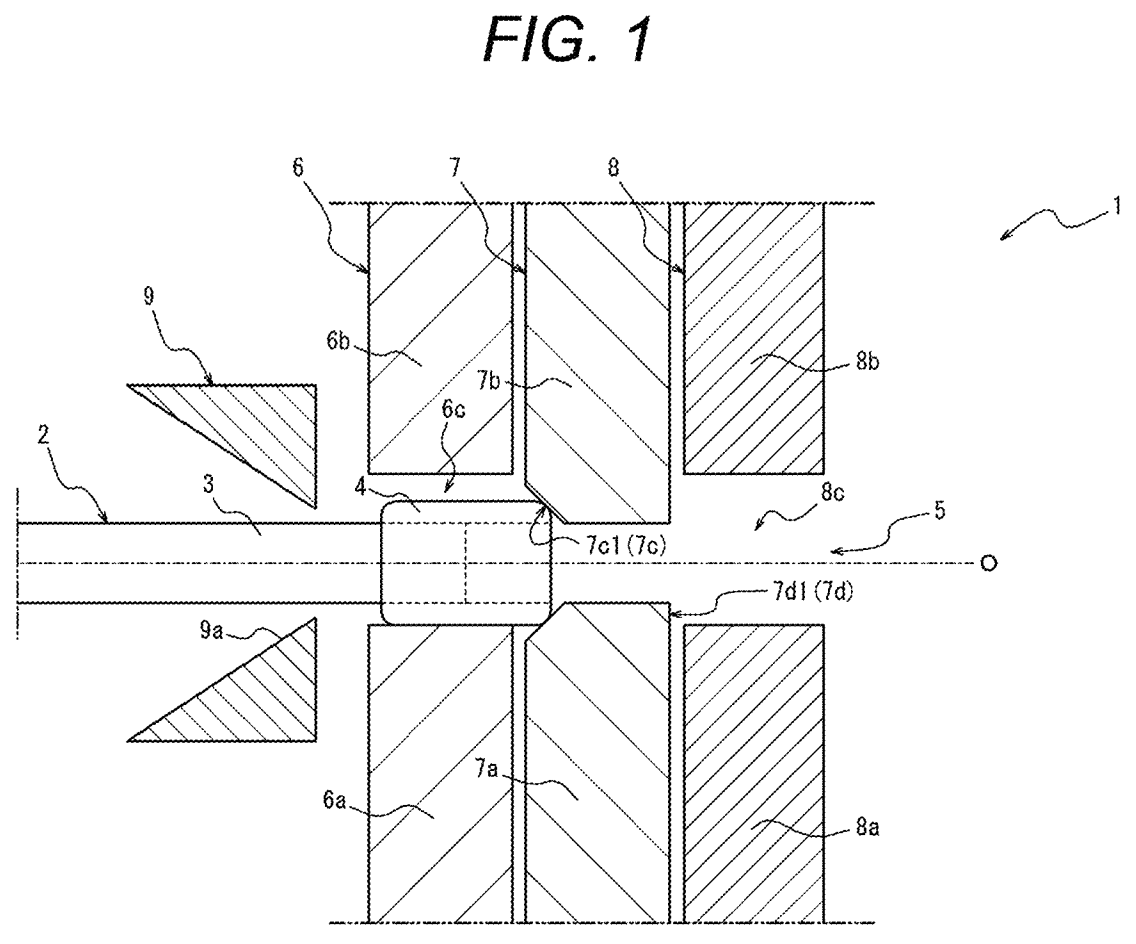
Figure 2:
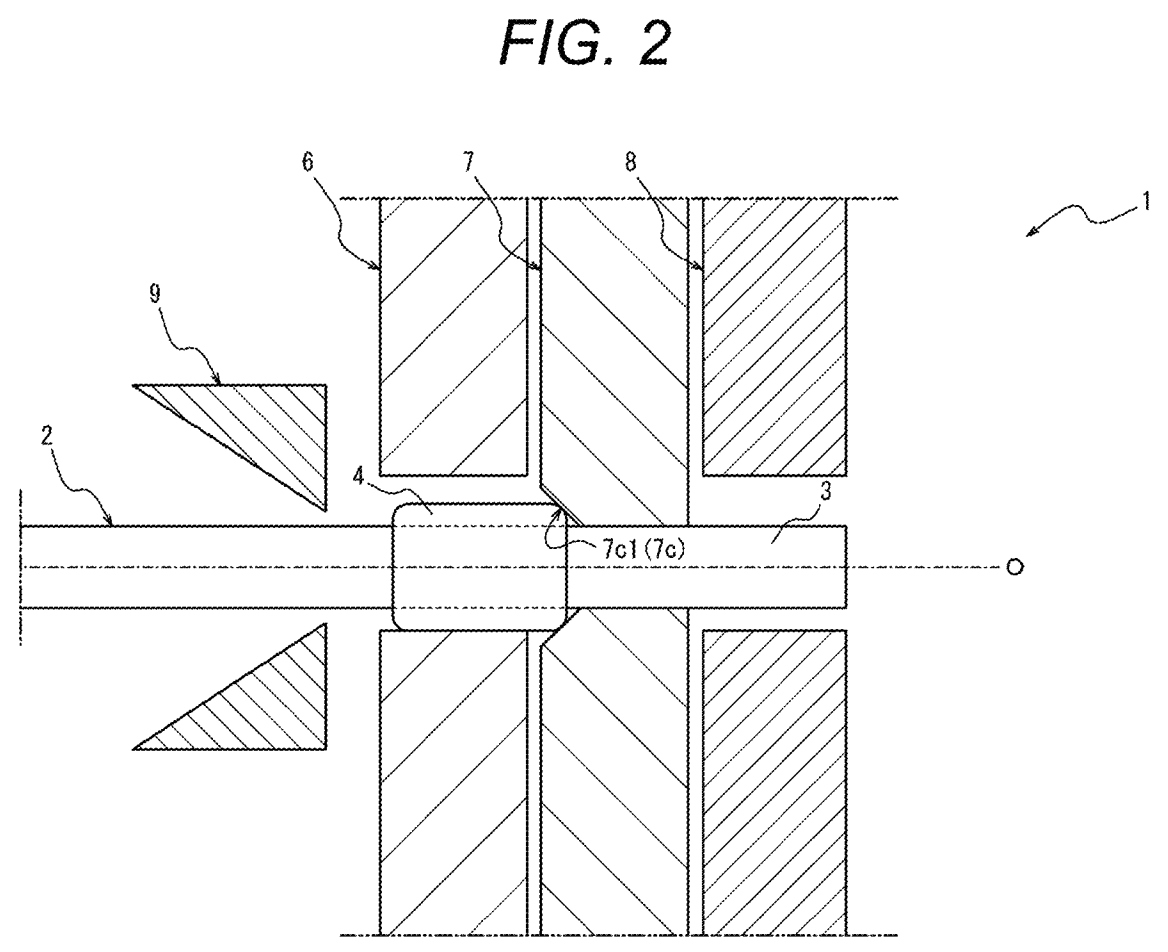
Figure 3:
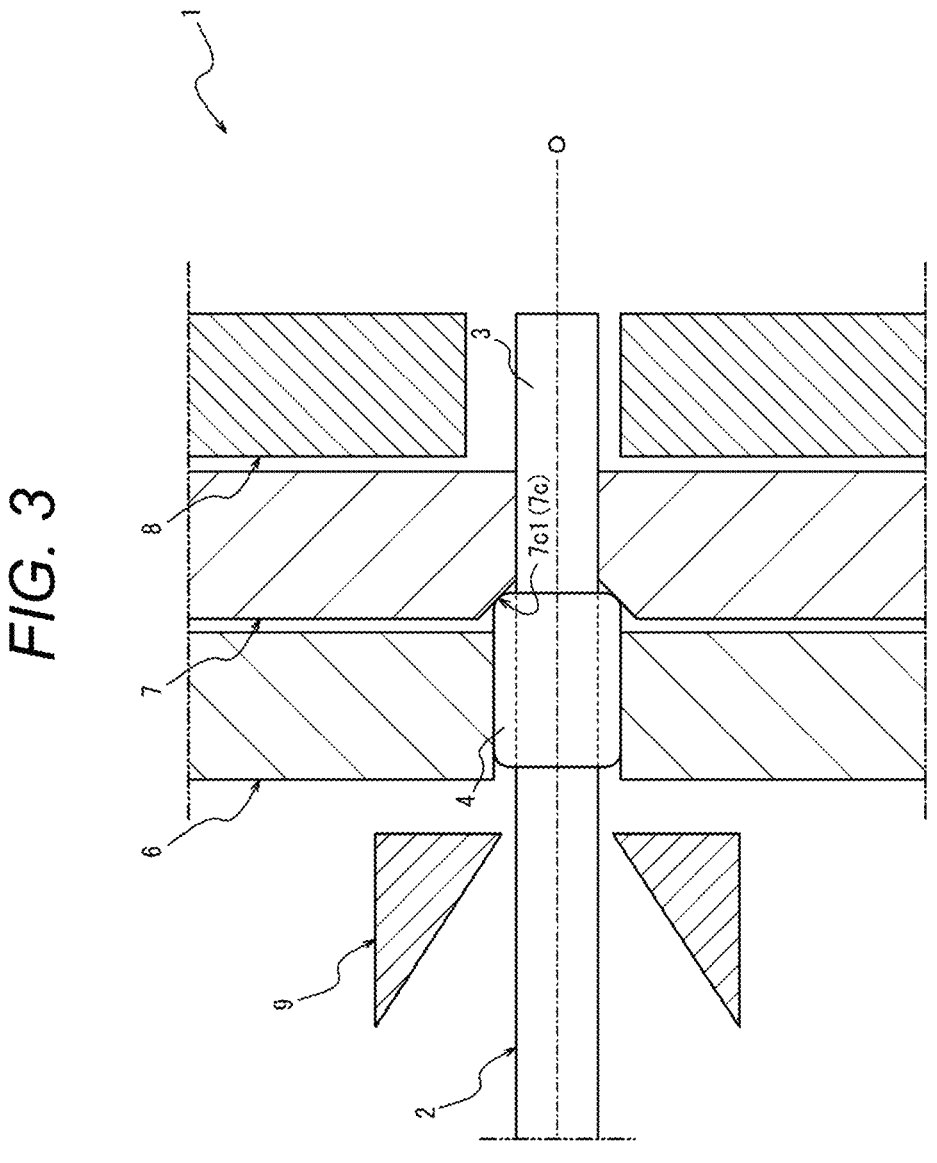
FIG. 3 is a sectional view illustrating a state where a first crimping step is performed after the state in FIG. 2.
Figure 4:
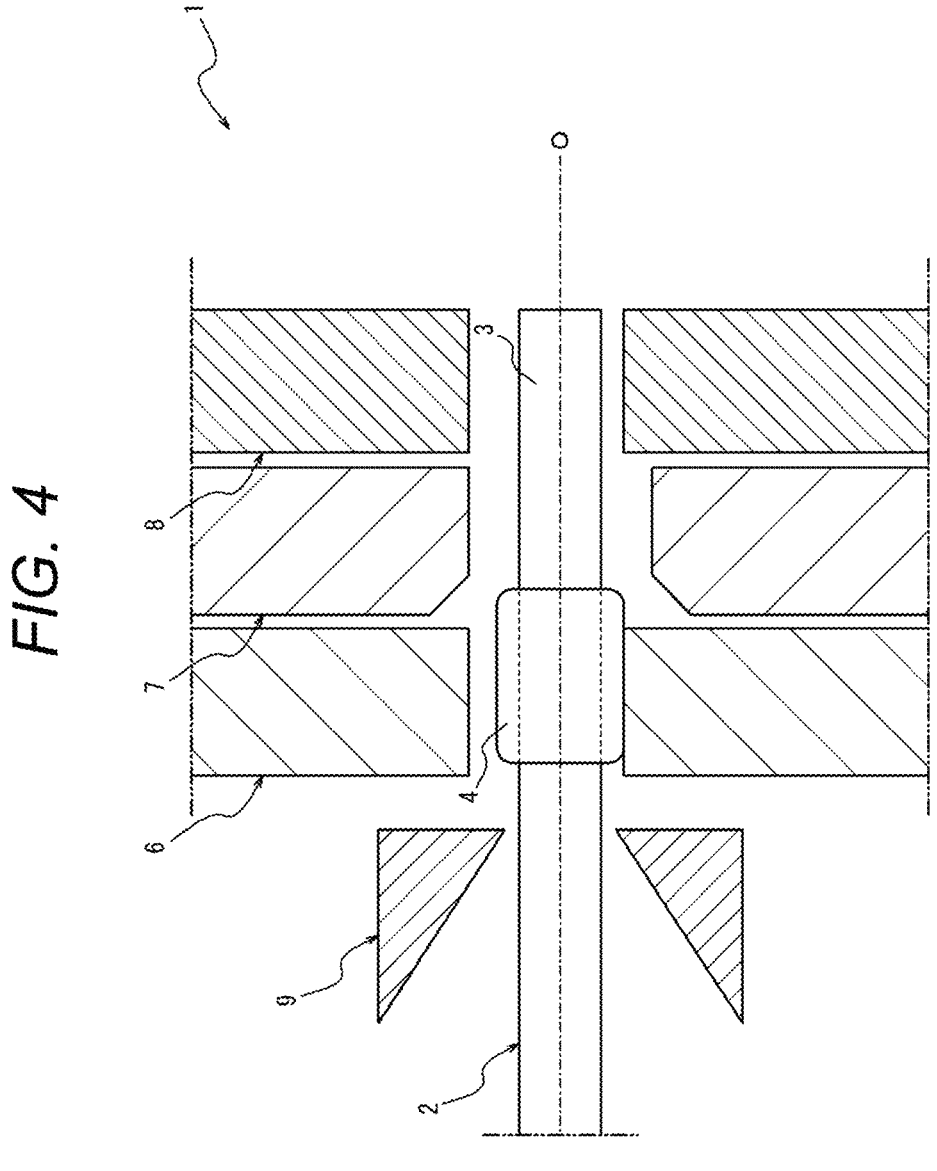
FIG. 4 is a sectional view illustrating a state where a positioning step starts after the state in FIG. 3.
Figure 5:
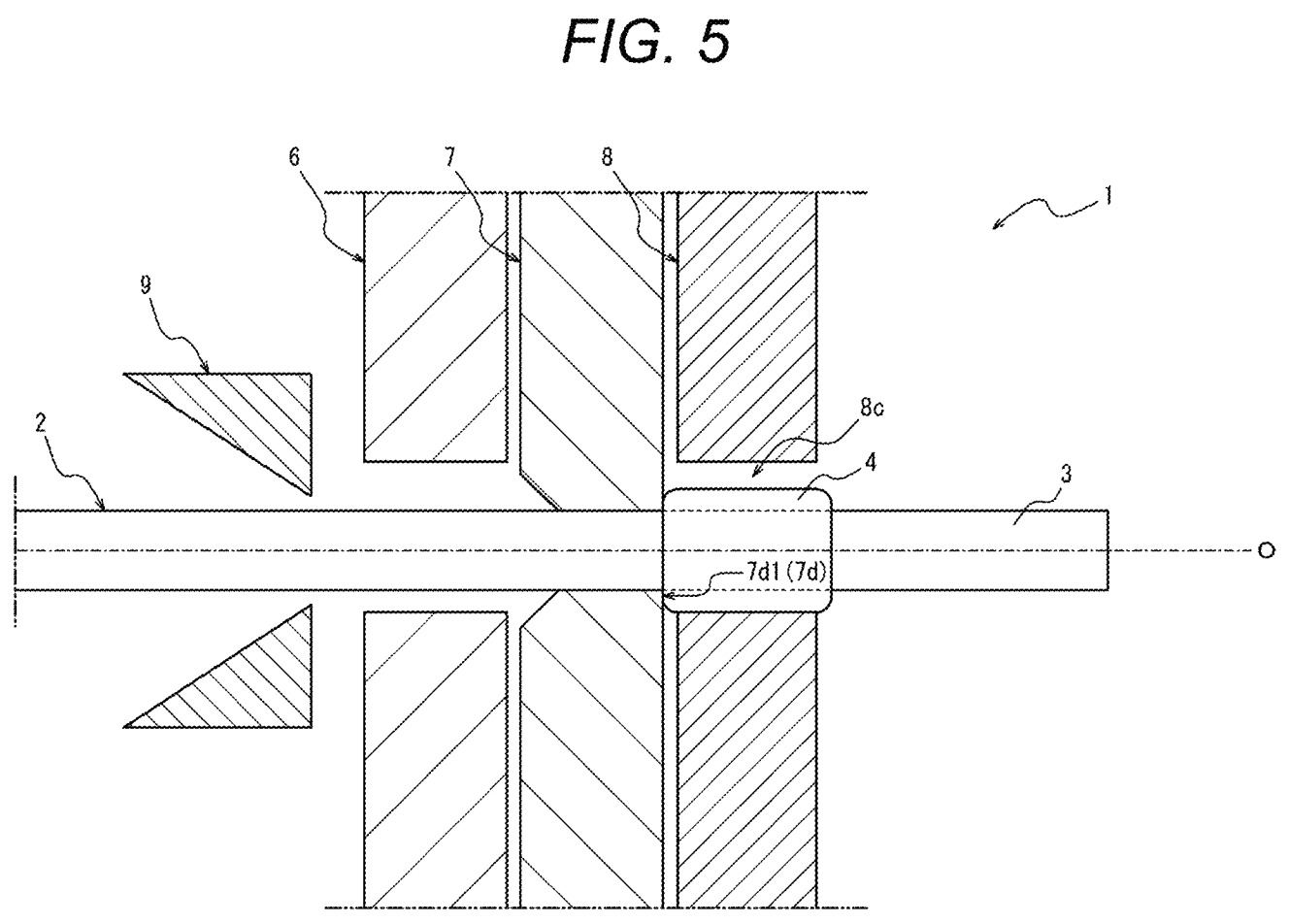
Figure 6:
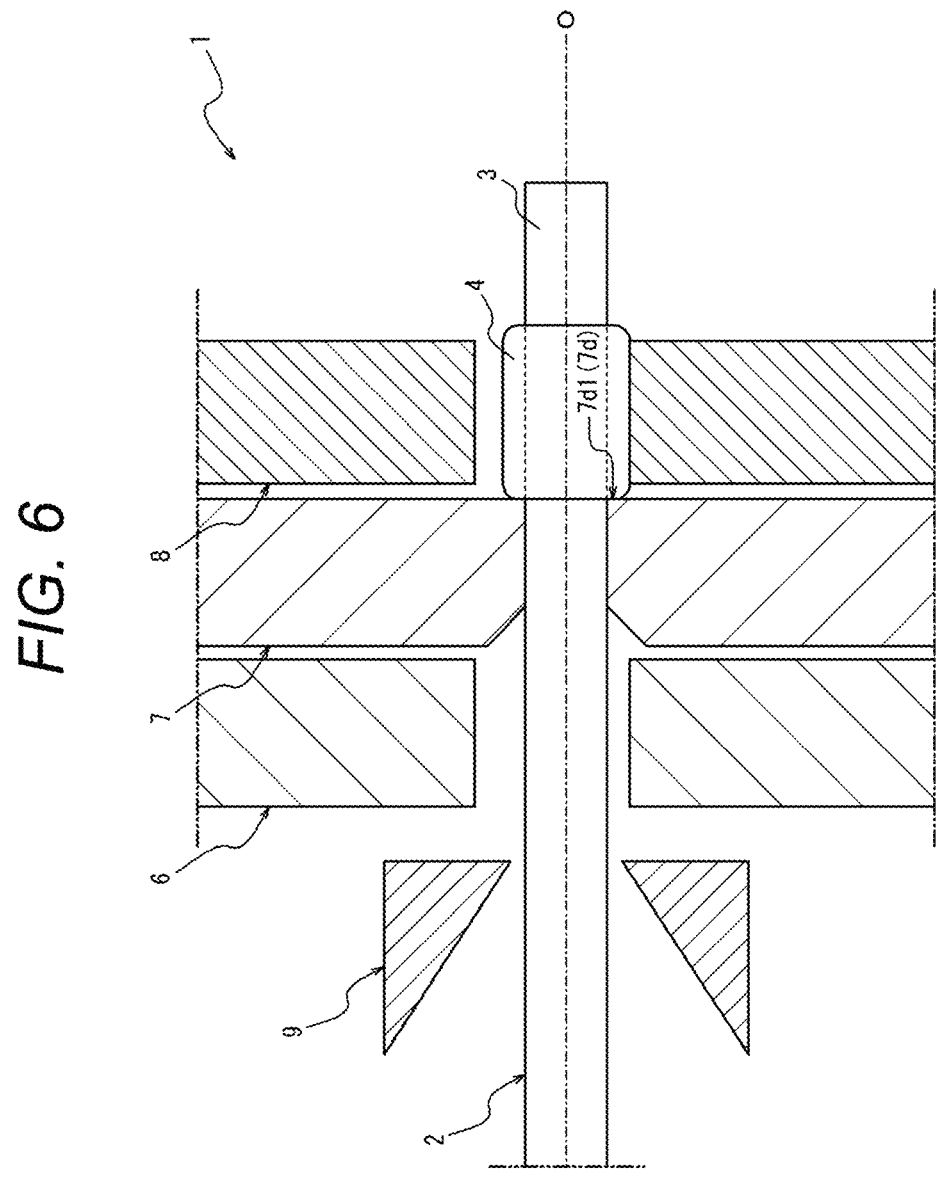
FIG. 6 is a sectional view illustrating a state where positioning of a cylindrical body is complete in the positioning step after the state in FIG. 5.
Figure 7:
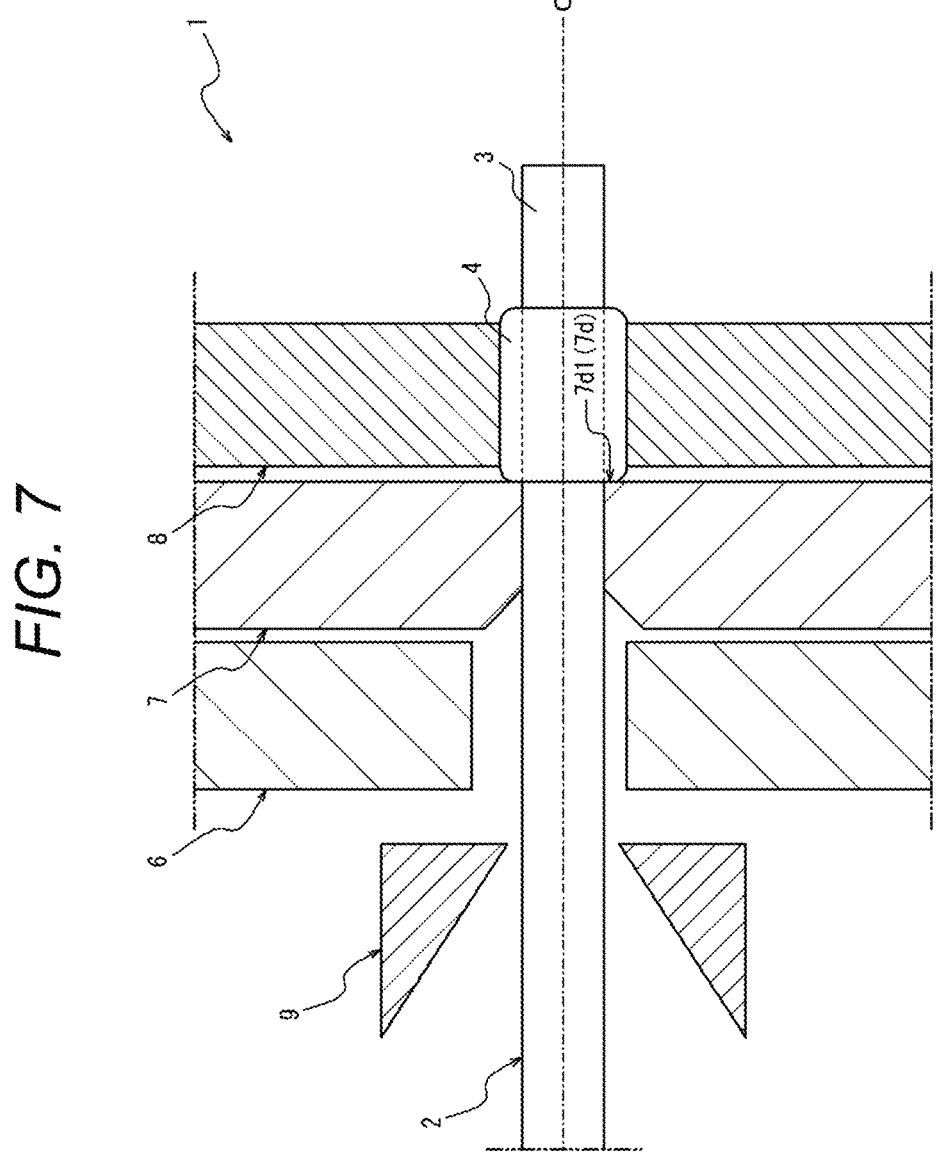
FIG. 7 is a sectional view illustrating a state where a second crimping step is performed after the state in FIG. 6.

As illustrated in FIGS. 1 to 7, a crimping device 1 according to an embodiment of the present disclosure is a crimping device 1 for crimping a cylindrical body 4 to a shaft member 3 of a catheter. A catheter is a medical instrument that is introduced into the body cavity of, for example, a patient. In the present embodiment, the cylindrical body 4 is a marker made of a material (for example, a metal) non-transmissive to X-rays.

The crimping device 1 includes a first crimping member 6, a positioning member 7, and a second crimping member 8. The first crimping member 6 is configured to perform first crimping to obtain a first crimped state where the cylindrical body 4 is crimped to the shaft member 3 with the cylindrical body that has the shaft member 3 inserted through the cylindrical body 4 and is fastened in a radial direction of the cylindrical body (see FIG. 3). The positioning member 7 is configured to perform a positioning operation (see FIGS. 4 to 6), where the positioning member 7 is provided ahead of the first crimping member 6 with a movement path 5 maintained for axially forward movement or axially backward movement of the shaft member 3. The positioning operation includes a radial operation in which the positioning member 7 operates radially inwardly (see FIG. 5), and a retaining operation that retains a position of the positioning member 7 after the radial operation (see FIG. 6). The radial operation is to be performed to obtain a contact state where the cylindrical body 4 has a rear end face in contact with the positioning member 7 in a case where the rear end face of the cylindrical body 4 in the first crimped state moves backward after passing the positioning member 7 forward (see FIG. 5). The retaining operation is to be performed to obtain a positioned state where the cylindrical body 4 is positioned to the shaft member 3 after the shaft member 3 moves backward with respect to the cylindrical body 4 in the contact state (see FIG. 6). The second crimping member 8 is provided ahead of the positioning member 7 with the movement path 5 maintained. The second crimping member 8 is configured to perform second crimping to obtain a second crimped state where the cylindrical body 4 is crimped more firmly than the cylindrical body 4 in the first crimped state, with the cylindrical body 4 in the positioned state and in the contact state that is fastened in the radial direction (see FIG. 7).

In the present application, a direction from the first crimping member 6 to the second crimping member 8 along an axial direction is defined as ahead of or forward and an opposite direction is defined as behind or backward for convenience of description. In the present embodiment, the axial direction is defined as a direction along the central axis O of the shaft member 3, a direction orthogonal to the central axis O is defined as a radial direction, and a direction around the central axis O is referred to as a circumferential direction.

The first crimping member 6 includes a first portion (or first member) 6a and a second portion (or second member) 6b that are relatively movable to each other between one side and the other side in the radial direction. The first crimping member 6 is configured to perform first crimping by moving the first portion 6a and the second portion 6b relatively to each other inward in the radial direction with respect to the cylindrical body 4 in a first retained state where the cylindrical body 4 is retained in a first retaining space 6c of the first crimping member 6 formed between the first portion 6a and the second portion 6b (see FIGS. 1 to 3). The positioning member 7 includes a first portion (first member) 7a and a second portion (second member) 7b that are relatively movable to each other between one side and the other side in the radial direction. The positioning member 7 is configured to perform a radial operation by moving the first portion 7a and the second portion 7b relatively to each other inward in the radial direction. The positioning member 7 is configured to perform a retaining operation by retaining the respective relative positions in the radial direction of the first portion 7a and the second portion 7b. The second crimping member 8 includes a first portion (first member) 8a and a second portion (second member) 8b that are relatively movable to each other between one side and the other side in the radial direction. The second crimping member 8 is configured to perform second crimping by moving the first portion 8a and the second portion 8b relatively to each other inward in the radial direction with respect to the cylindrical body 4 in a second retained state where the cylindrical body 4 is retained in a second retaining space 8c of the second crimping member 8 formed between the first portion 8a and the second portion 8b (see FIGS. 5 to 7).

The crimping device 1 further includes a guide member 9 disposed behind the first crimping member 6. The guide member 9 has a guide face 9a that guides the front end of the shaft member 3 into the cylindrical body 4 in the first retained state when the shaft member 3 moves forward. The guide face 9a is frustoconical in shape and has a diameter decreasing forward, but is not limited to the frustoconical shape with the diameter decreasing forward.

The second portion 6b of the first crimping member 6 is movable between one side and the other side in the radial direction with respect to the first portion 6a in the stationary state. The first crimping member 6 is configured to perform the first crimping by moving the second portion 6b inward in the radial direction toward the first portion 6a in the stationary state with respect to the cylindrical body 4 in the first retained state. The first crimping member 6 is not limited to the above configuration. For example, the first portion 6a and the second portion 6b may be movable between one side and the other side in the radial direction, and the first crimping member 6 may be configured to perform first crimping by moving the first portion 6a and the second portion 6b inward in the radial direction with respect to the cylindrical body 4 in the first retained state.

The first portion 7a and the second portion 7b of the positioning member 7 are movable between one side and the other side in the radial direction. The positioning member 7 is configured to perform the radial operation by moving the first portion 7a and the second portion 7b inward in the radial direction, and is configured to perform the retaining operation by retaining the respective positions in the radial direction of the first portion 7a and the second portion 7b. The positioning member 7 is not limited to the above configuration. For example, the second portion 7b may be movable between one side and the other side in the radial direction toward the first portion 7a in the stationary state. The positioning member 7 may be configured to perform a radial operation by moving the second portion 7b inward in the radial direction toward the first portion 7a in the stationary state, and may be configured to perform a retaining operation by retaining the position in the radial direction of the second portion 7b with respect to the first portion 7a in the stationary state.

The second portion 8b of the second crimping member 8 is movable between one side and the other side in the radial direction toward the first portion 8a in the stationary state. The second crimping member 8 is configured to perform the second crimping by moving the second portion 8b inward in the radial direction toward the first portion 8a with respect to the cylindrical body 4 in the second retained state. The second crimping member 8 is not limited to the above configuration. For example, the first portion 8a and the second portion 8b may be movable between one side and the other side in the radial direction. The second crimping member 8 may be configured to perform the second crimping by moving the first portion 8a and the second portion 8b inward in the radial direction with respect to the cylindrical body 4 in the second retained state.

The first crimping member 6 is configured to retain the cylindrical body 4 in the first retaining space 6c by placing the cylindrical body 4 before the shaft member 3 is inserted through the cylindrical body 4, on the first portion 6a in the stationary state. The means for retaining the cylindrical body 4 in the first retaining space 6c before the shaft member 3 is inserted through the cylindrical body 4 is not limited to the means described above.

The positioning member 7 includes a restricting portion 7c that has contact with the front end face of the cylindrical body 4 placed on the first portion 6a of the first crimping member 6 such that an inclination of the cylindrical body 4 is restricted with respect to the shaft member 3 when the shaft member 3 moves forward to be inserted into the cylindrical body 4. In the present embodiment, the restricting portion 7c extends all over in the circumferential direction. The restricting portion 7c is provided over half the circumference of the first portion 7a of the positioning member 7 and over half the circumference of the second portion 7b of the positioning member 7. The restricting portion 7c is not limited to the configuration in which the restricting portion 7c extends all over in the circumferential direction, and may be, for example, provided at two or more parts of the positioning member 7 in the circumferential direction. The two or more parts at which the restricting portion 7c is provided may be located at regular intervals (i.e., the two or more parts are at defined or predetermined intervals). In the present embodiment, the restricting portion 7c includes a chamfered portion 7c1 having a diameter decreasing forward. Because the positioning member 7 includes the restricting portion 7c, the shaft member 3 moves forward after the cylindrical body 4 has contact with the restricting portion 7c. Therefore, the first crimping is performed with the longitudinal axis (central axis O) of the shaft member 3 and the longitudinal axis of the cylindrical body 4 in parallel or coaxial. As a result, the inclination of the longitudinal axis of the cylindrical body 4 with respect to the longitudinal axis of the shaft member 3 is reduced, whereby the shift of the position where the first crimping is performed can be prevented.

The first crimping member 6 is configured to perform the first crimping by fastening the cylindrical body 4 in the radial direction in the first retained state, the cylindrical body 4 having the shaft member 3 inserted through the cylindrical body 4. The cylindrical body 4 being placed on the first portion 6a of the first crimping member 6 and the cylindrical body 4 being in contact with the restricting portion 7c of the positioning member 7. In the present embodiment, the positioning member 7 is configured to perform an opening operation in which the positioning member 7 moves outward in the radial direction after the first crimping is performed and before the positioning operation is performed. The opening operation is performed due to radial outward movement of the first portion 7*a* and the second portion 7*b*. The positioning member 7 is configured to perform the radial operation in a case where the cylindrical body 4 in the first crimped state has passed the positioning member 7 forward after the opening operation. After the positioning member 7 moves radially inwardly due to the radial operation, the retaining operation for retaining the position of the positioning member 7 is performed. The shaft member 3 moves backward together with the cylindrical body 4 in the first crimped state, so that the rear end face of the cylindrical body 4 has contact with a contact portion 7*d* on the front end face of the positioning member 7 during the retaining operation. The shaft member 3 further moves backward in this state, so that the cylindrical body 4 in the first crimped state relatively moves to the target position for positioning while being slid over the shaft member 3. The cylindrical body 4 in the positioned state where the positioning is performed as described above is subjected to the second crimping while the contact of the cylindrical body 4 with the contact portion 7*d* is maintained. As a result, the cylindrical body 4 is positioned.

In the present embodiment, the contact portion 7*d* of the positioning member 7 extends all over in the circumferential direction. The contact portion 7*d* is provided over half the circumference of the first portion 7*a* of the positioning member 7 and over half the circumference of the second portion 7*b* of the positioning member 7. The contact portion 7*d* is not limited to the configuration in which the contact portion 7*d* extends entirely over in the circumferential direction, and may be provided, for example, at two or more parts of the positioning member 7 in the circumferential direction. The two or more parts at which the contact portion 7*d* is provided may be located at regular intervals (i.e., the two or more parts are at defined or predetermined intervals). In the present embodiment, the contact portion 7*d* can include an annular flat face 7*d*1 perpendicular to the axial direction.

In the present embodiment, a shaft 2 including a shaft member 3 for a catheter and a cylindrical body 4 crimped to the shaft member 3 is manufactured using the crimping device 1.

The shaft manufacturing method includes a first crimping step of performing first crimping by the first crimping member 6, a positioning step of performing a positioning operation by the positioning member 7, and a second crimping step of performing second crimping by the second crimping member 8.

The shaft manufacturing method further includes an inserting step of moving the shaft member 3 forward to insert the shaft member 3 into the cylindrical body 4 before the first crimping step, and the positioning member 7 includes the restricting portion 7*c* that has contact with the front end face of the cylindrical body 4 such that an inclination of the cylindrical body 4 is restricted with respect to the shaft member 3 in the inserting step.

The shaft manufacturing method further includes a guiding step of guiding the front end of the shaft member 3 by the guide face 9*a* of the guide member 9 before the inserting step.

According to the present embodiment, the positioning step is performed after the followability of the cylindrical body 4 to the shaft member 3 is increased in the first crimping step. Therefore, a decrease in positioning accuracy due to non-following of the cylindrical body 4 to the shaft member 3 can be prevented resulting from catching on (or being entangled with), for example, the second crimping member 8 when the shaft member 3 moves backward in the positioning step.

The embodiments of the present disclosure have been described above. The present disclosure, however, is not limited to the above-described embodiments, and thus the above-described embodiments can be variously modified without departing from the gist of the present disclosure.

For example, in the above-described embodiments, the guide member 9 is disposed behind the first crimping member 6, and the guiding step and the inserting step are performed by moving the shaft member 3 forward. However, the present disclosure is not limited to the configuration. The guide member 9 may be disposed ahead of the second crimping member 8, the guiding step and the inserting step may be performed by moving the shaft member 3 backward, the first crimping step and the subsequent steps may be performed in the manner similar to that in the above-described embodiments, and the guide member 9 may have a guide face 9*a* that guides the rear end of the shaft member 3 into the cylindrical body 4 in the first retained state when the rear end of the shaft member 3 moves backward.

The detailed description above describes embodiments of a crimping device and a shaft manufacturing method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A crimping device for crimping a cylindrical body to a shaft member for a catheter, the crimping device comprising:

a first crimping member configured to perform first crimping to obtain a first crimped state where the cylindrical body is crimped to the shaft member with the cylindrical body that has the shaft member inserted through the cylindrical body and is fastened in a radial direction of the cylindrical body;

a positioning member configured to perform a positioning operation, the positioning member being provided ahead of the first crimping member with a movement path maintained for axially forward movement or axially backward movement of the shaft member, the positioning operation including:

a radial operation in which the positioning member operates radially inwardly; and a retaining operation that retains a position of the positioning member after the radial operation, the radial operation being to be performed to obtain a contact state where the cylindrical body has a rear end face in contact with the positioning member in a case where the rear end face of the cylindrical body in the first crimped state moves backward after passing the positioning member forward, the retaining operation being to be performed to obtain a positioned state where the cylindrical body is positioned to the shaft member after the shaft member moves backward with respect to the cylindrical body in the contact state; and a second crimping member provided ahead of the positioning member with the movement path maintained, the second crimping member being configured to perform second crimping to obtain a second crimped state where the cylindrical body is crimped more firmly than the cylindrical body in the first crimped state, with the cylindrical body in the positioned state and in the contact state that is fastened in the radial direction of the cylindrical body.

2. The crimping device according to claim 1, wherein the positioning member includes a restricting portion that is configured to contact a front end face of the cylindrical body such that an inclination of the cylindrical body is restricted with respect to the shaft member when the shaft member moves forward to be inserted into the cylindrical body.

3. The crimping device according to claim 2, wherein the restricting portion includes a chamfered portion having a diameter decreasing in a forward direction.

4. The crimping device according to claim 3, wherein the positioning member is provided such that the restricting portion is configured to contact an entire circumference of the cylindrical body.

5. The crimping device according to claim 3, wherein the restricting portion of the positioning member is provided to have contact with at least two parts in a circumferential direction of the cylindrical body.

6. The crimping device according to claim 5, wherein the at least two parts with which the restricting portion of the positioning member is to have contact are located at regular intervals in the circumferential direction of the cylindrical body.

7. The crimping device according to claim 1, further comprising:

a guide member disposed behind the first crimping member, the guide member having a guide face that guides a front end of the shaft member into the cylindrical body when the shaft member moves forward.

8. The crimping device according to claim 7, wherein the guide face is frustoconical in shape and has a diameter decreasing in a forward direction.

9. The crimping device according to claim 1, wherein the cylindrical body is a marker made of a material that is non-transmissive to X-rays.

10. A shaft manufacturing method for manufacturing a shaft including the shaft member for the catheter and the cylindrical body crimped to the shaft member using the crimping device according to claim 1, the method comprising:

performing the first crimping by the first crimping member;

performing the positioning operation by the positioning member; and performing the second crimping by the second crimping member.

11. The shaft manufacturing method according to claim 10, further comprising:

moving the shaft member forward to insert the shaft member into the cylindrical body before the first crimping by the first crimping member, and wherein the positioning member includes a restricting portion that has contact with a front end face of the cylindrical body such that an inclination of the cylindrical body is restricted with respect to the shaft member in the moving of the shaft member forward to insert the shaft member into the cylindrical body before the first crimping by the first crimping member.

12. A crimping device for crimping a cylindrical body of a non-transmissive material to X-rays to a shaft member for a catheter, the crimping device comprising:

a first crimping member, the first crimping member including a first portion and a second portion configured to perform a first crimping where the cylindrical body is crimped to the shaft member to obtain a first crimped state;

a positioning member, the positioning member including a first portion and a second portion configured to the cylindrical body on the shafter member; and a second crimping member, the second crimping member including a first portion and a second portion configured to perform a second crimping of the cylindrical body to the shaft member, and wherein the second crimping of the cylindrical body is performed after the first crimping of the cylindrical body to obtain a second crimped state.

13. The crimping device according to claim 12, wherein the positioning member is configured to perform a positioning operation comprising:

a radial operation in which the positioning member operates radially inwardly; and a retaining operation that retains a position of the positioning member after the radial operation, the radial operation being to be performed to obtain a contact state where the cylindrical body has a rear end face in contact with the positioning member in a case where the rear end face of the cylindrical body in the first crimped state moves backward after passing the positioning member forward, the retaining operation being to be performed to obtain a positioned state where the cylindrical body is positioned to the shaft member after the shaft member moves backward with respect to the cylindrical body in the contact state.

14. The crimping member according to claim 12, wherein the positioning member is provided ahead of the first crimping member with a movement path for an axial movement of the shaft member in an axially forward direction and an axially backward direction; and the second crimping member is provided ahead of the positioning member with the movement path for the axial movement of the shaft member in the axially forward direction and the axially backward direction.

15. The crimping device according to claim 12, wherein the positioning member includes a chamfered portion that is configured to contact a front end face of the cylindrical body such that an inclination of the cylindrical body is restricted with respect to the shaft member when the shaft member moves forward to be inserted into the cylindrical body.

16. The crimping device according to claim 12, further comprising:

a guide member disposed behind the first crimping member, the guide member having a guide face that guides a front end of the shaft member into the cylindrical body when the shaft member moves forward.

17. The crimping device according to claim 16, wherein the guide face is frustoconical in shape and has a diameter decreasing in a forward direction.

18. A method for manufacturing a shaft including a shaft member for a catheter and a cylindrical body crimped to the shaft member, the method comprising:

performing a first crimping of the cylindrical body to the shaft member to obtain a first crimped state where the cylindrical body is crimped to the shaft member with the cylindrical body that has the shaft member inserted through the cylindrical body and is fastened in a radial direction of the cylindrical body;

performing a positioning operation with a positioning member that is arranged ahead of the first crimping member with a movement path for axially forward movement or axially backward movement of the shaft member, the positioning operation including:

a radial operation in which the positioning member operates radially inwardly; and a retaining operation that retains a position of the positioning member after the radial operation, the radial operation being to be performed to obtain a contact state where the cylindrical body has a rear end face in contact with the positioning member in a case where the rear end face of the cylindrical body in the first crimped state moves backward after passing the positioning member forward, the retaining operation being to be performed to obtain a positioned state where the cylindrical body is positioned to the shaft member after the shaft member moves backward with respect to the cylindrical body in the contact state; and performing a second crimping operation with a second crimping member provided ahead of the positioning member with the movement path, the second crimping member being configured to perform a second crimping to obtain a second crimped state where the cylindrical body is crimped more firmly than the cylindrical body in the first crimped state, with the cylindrical body in the positioned state and in the contact state that is fastened in the radial direction of the cylindrical body.

19. The method according to claim 18, further comprising:

moving the shaft member forward to insert the shaft member into the cylindrical body before the first crimping of the cylindrical body to the shaft member, and restricting a movement of the cylindrical body with respect to the shaft member in the moving of the shaft member forward to insert the shaft member into the cylindrical body before the first crimping by the first crimping member with the positioning member.

20. The method according to claim 18, further comprising:

guiding a front end of the shaft member into the cylindrical body when the shaft member moves forward with a guide member disposed behind the first crimping member.

\* \* \* \* \*